US010240768B1

(12) United States Patent
Foster

(10) Patent No.: US 10,240,768 B1
(45) Date of Patent: Mar. 26, 2019

(54) LIGHT FIXTURE PANNING APPARATUS

(71) Applicant: Electronic Theatre Controls, Inc., Middleton, WI (US)

(72) Inventor: Cary Foster, Middleton, WI (US)

(73) Assignee: Electronic Theatre Controls, Inc., Middleton, WI (US)

( * ) Notice: Subject to any disclaimer, the term of this patent is extended or adjusted under 35 U.S.C. 154(b) by 0 days.

(21) Appl. No.: 15/861,995

(22) Filed: Jan. 4, 2018

(51) Int. Cl.

| | |
|---|---|
| ***A61B 17/3207*** | (2006.01) |
| ***F21V 21/30*** | (2006.01) |
| ***F21V 21/04*** | (2006.01) |
| ***F21S 8/02*** | (2006.01) |
| ***F21V 19/00*** | (2006.01) |
| *F21Y 115/10* | (2016.01) |

(52) U.S. Cl.
CPC ................ *F21V 21/30* (2013.01); *F21S 8/02* (2013.01); *F21V 19/001* (2013.01); *F21V 21/04* (2013.01); *F21Y 2115/10* (2016.08)

(58) Field of Classification Search
CPC ........ A61B 17/320725; A61B 17/3209; A61B 17/32075; A61B 2017/00986
See application file for complete search history.

(56) References Cited

U.S. PATENT DOCUMENTS

| | | | | |
|---|---|---|---|---|
| 2,779,642 | A | 1/1957 | Matthews | |
| 2,867,145 | A | 1/1959 | Markstrum | |
| 2,933,242 | A | 4/1960 | Wright et al. | |
| 3,192,422 | A | 6/1965 | Kober | |
| 4,827,387 | A * | 5/1989 | Ferren | F21S 10/06 362/277 |
| 4,909,644 | A | 3/1990 | Owens | |
| 6,050,741 | A | 4/2000 | Aultman et al. | |
| 8,831,415 | B2 | 9/2014 | Greenthal | |
| 9,719,560 | B2 | 8/2017 | Dreizler et al. | |
| 2014/0123789 | A1 | 5/2014 | Saunders et al. | |
| 2015/0276190 | A1 * | 10/2015 | Devlin | F21V 21/15 362/362 |

FOREIGN PATENT DOCUMENTS

| | | |
|---|---|---|
| JP | H-08334125 | 12/1996 |

* cited by examiner

*Primary Examiner* — David V Bruce
(74) *Attorney, Agent, or Firm* — Michael Best & Friedrich LLP

(57) ABSTRACT

A light fixture panning apparatus including a base, a light fixture rotatably coupled to the base such that the light fixture rotates about an axis relative to the base, and a bearing that facilitates rotation of the light fixture relative to the base about the axis. The bearing includes a raceway and a rolling element that rolls along the raceway as the light fixture rotates about the axis relative to the base. The raceway is curved such that the raceway extends around at least a portion of the axis.

20 Claims, 3 Drawing Sheets

LIGHT FIXTURE PANNING APPARATUS

BACKGROUND

The present invention relates to lighting and more particularly to an apparatus for panning a light fixture.

In lighting applications, such as theatre lighting, it is desirable to rotate or pan a light source. A panning apparatus may include a motor and controls to automatically pan the light source so that the light source illuminates a desired object or area. Cables associated with the motor, controls, and/or light source run along or through the panning apparatus. Rotation of the light source may then need to be limited so that the cables do not twist beyond a desired limit. Therefore, light fixture panning apparatus may include a rotational stop to stop rotation of the light source beyond a desired degree of rotation.

SUMMARY

In one embodiment, the invention provides a light fixture panning apparatus including a base, a light fixture rotatably coupled to the base such that the light fixture rotates about an axis relative to the base, and a bearing that facilitates rotation of the light fixture relative to the base about the axis. The bearing includes a raceway and a rolling element that rolls along the raceway as the light fixture rotates about the axis relative to the base. The raceway is curved such that the raceway extends around at least a portion of the axis.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Figure 1:
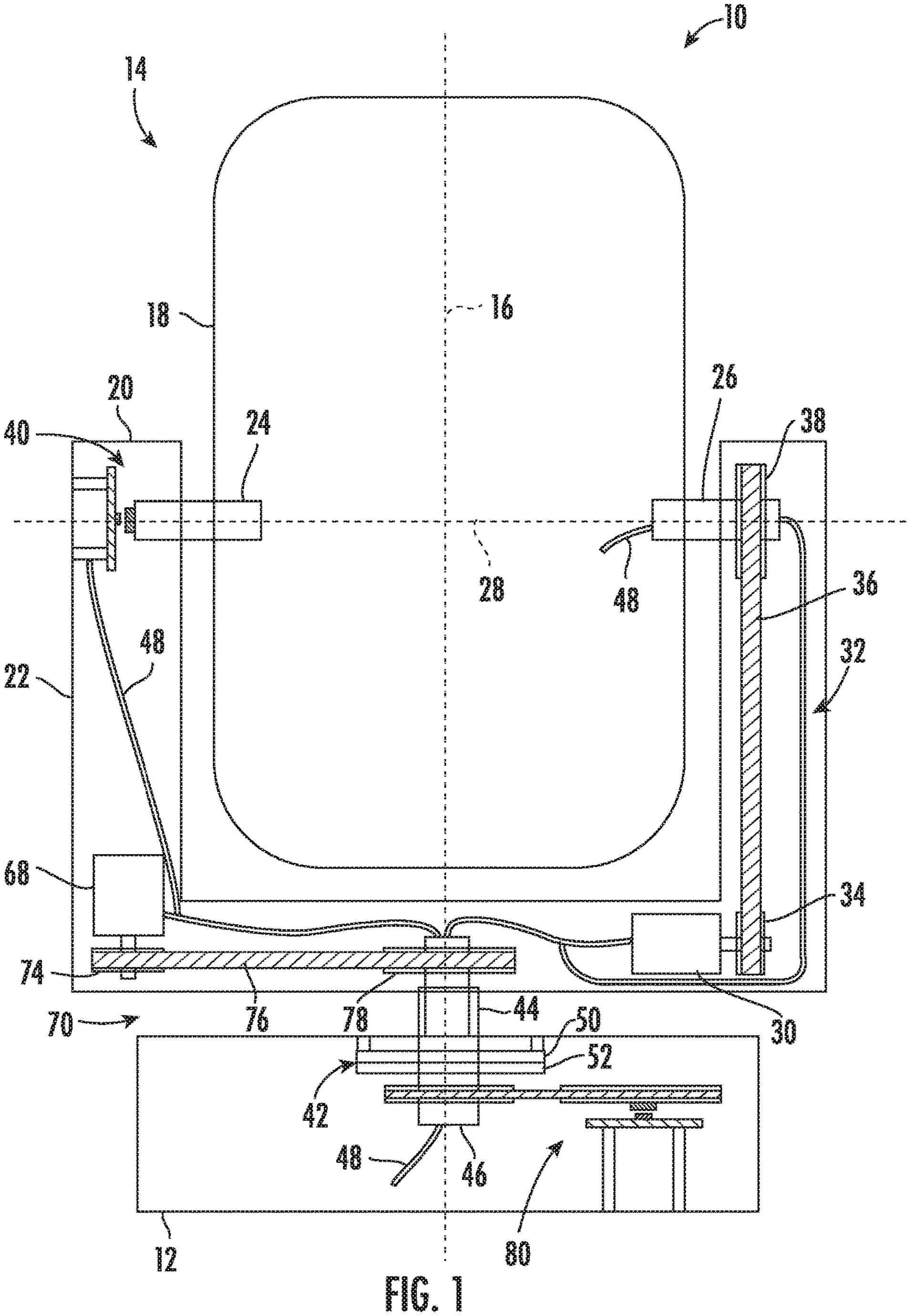
FIG. 1 illustrates a light fixture panning apparatus according to one possible embodiment of the invention.

FIG. 1 illustrates a light fixture panning apparatus 10. The panning apparatus 10 includes a base 12 and a light fixture 14. The light fixture panning apparatus 10 is operable to rotate or pan the light fixture 14 relative to the base 12 about a pan axis 16. The base 12 can be fixed to a floor, stage, batten, rigging equipment, trusses, beams and the like.

The light fixture 14 includes a light source 18 and a mount 20. The light source 18 can include any suitable type of light source or luminaire. For example, in one embodiment, the light source 18 includes a light emitting diode light source, such as a SOURCE FOUR® LED luminaire available from Electronic Theatre Controls. In other embodiments, other types of light sources can be utilized, such as incandescent light bulbs and the like.

The illustrated mount 20 includes a yoke 22, but in other embodiments, other shapes and types of mounts can be used. The yoke 22 couples the light source 18 to the base 12. The mount 20 further includes a first tilt shaft 24 and a second tilt shaft 26 that couple the light source 18 to yoke 22 for rotation of the light source 18 relative to the yoke 22 about a tilt axis 28. The tilt axis 28 is perpendicular to the pan axis 16. The illustrated panning apparatus 10 includes a tilt motor 30 and a tilt transmission 32. The illustrated tilt transmission 32 includes a drive pulley 34, a belt 36, and a driven pulley 38. The tilt motor 30 is operable to rotate the pulley 34, which rotates pulley 38 via the belt 36 in order to rotate the light source 18 relative to the yoke 22 about the tilt axis 28. The illustrated panning apparatus 10 further includes a tilt sensor 40. The tilt sensor 40 determines the degree or angle of tilt of the light source 18.

Figure 2:
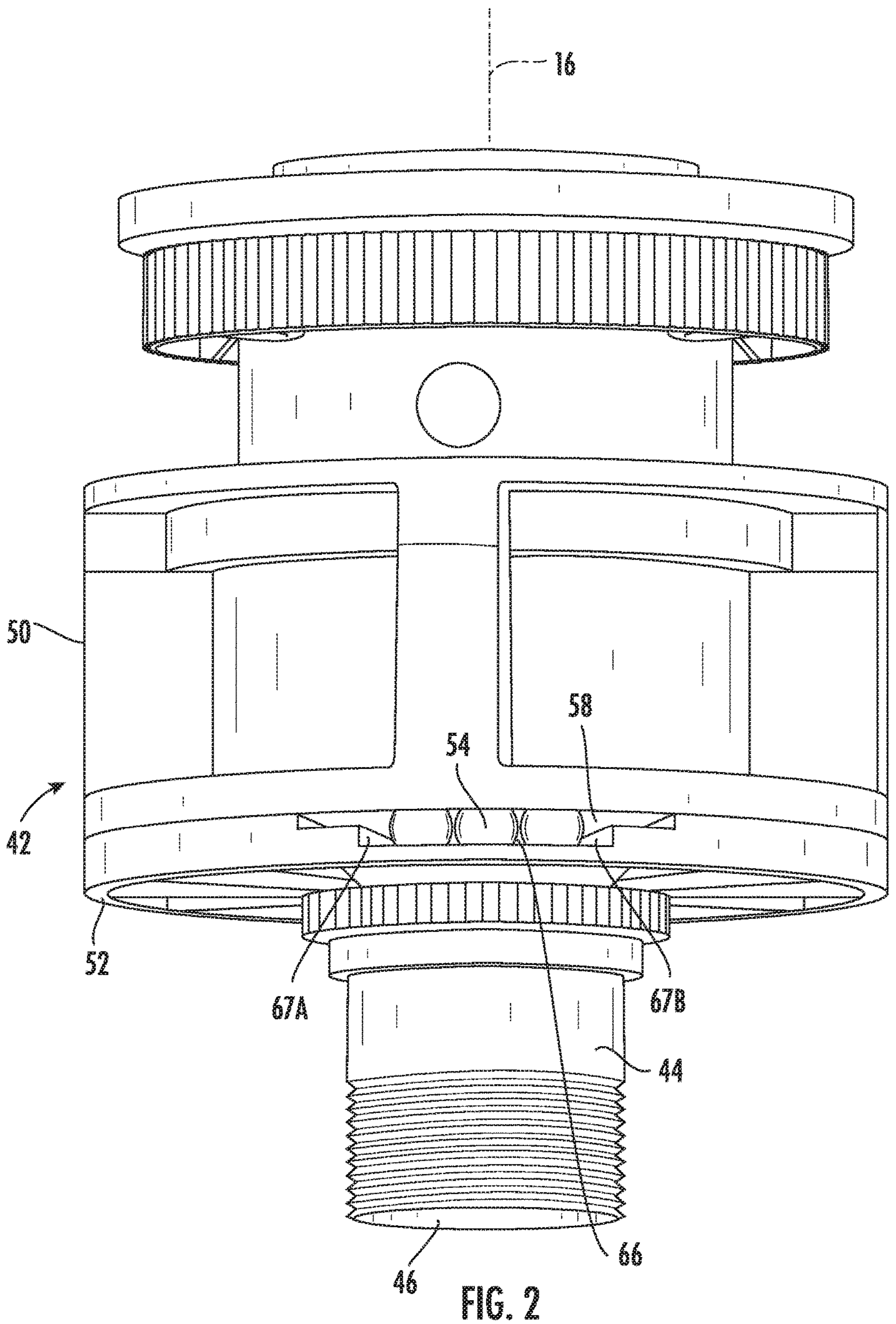
FIG. 2 illustrates a bearing of the light fixture panning apparatus of FIG. 1.
Figure 3:
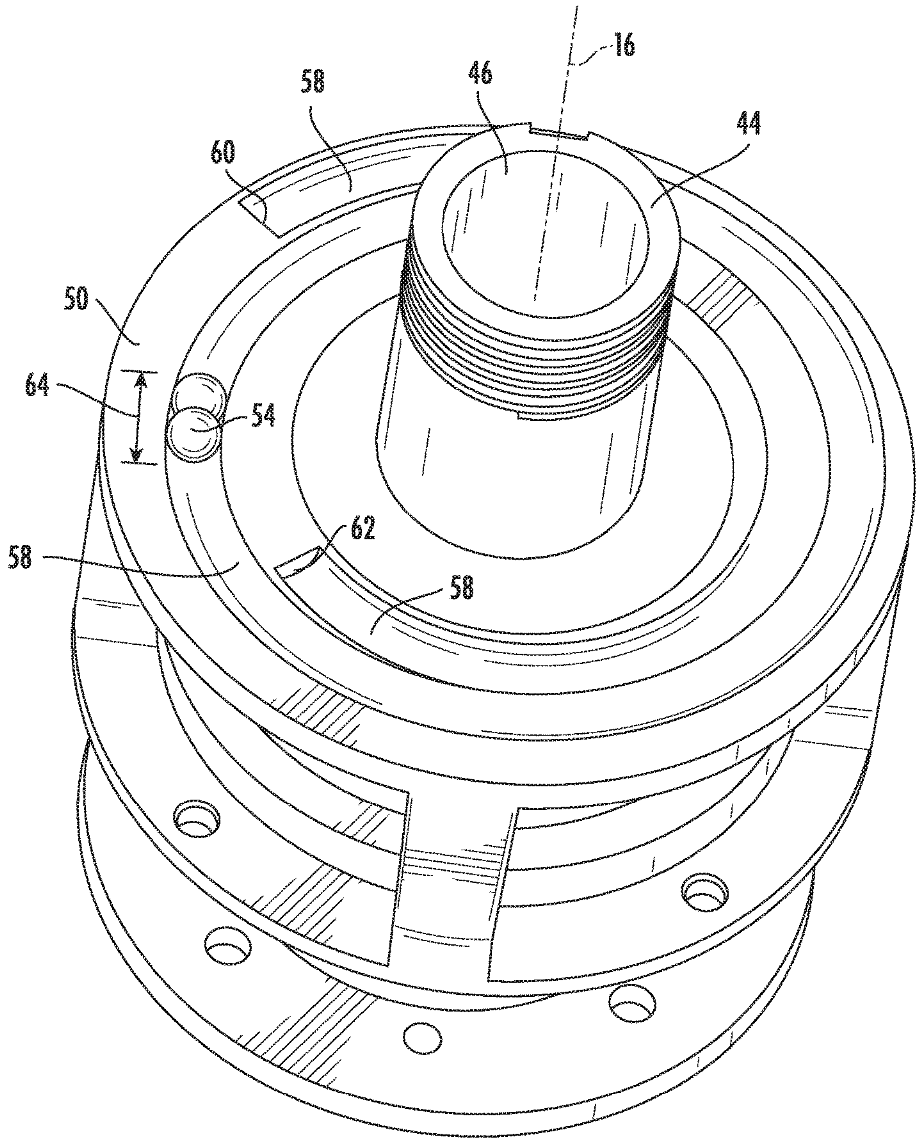
FIG. 3 is an alternative view of the bearing of FIG. 2.

The light fixture panning apparatus 10 further includes a bearing 42 that facilitates rotation of the light fixture 14 relative to the base 12 about the pan axis 16. As will be discussed in more detail below, the bearing 42 functions as a rotational stop to limit rotation of the light fixture 14 relative to the base 12. In the illustrated embodiment, the apparatus 10 includes a pan shaft 44 that rotationally couples the light fixture 14 to the base 12. The pan axis 16 extends centrally through the shaft 44 along a length of the shaft 44. As shown in FIGS. 2 and 3, the pan shaft 44 is hollow and includes an aperture 46 that extends along the length of the shaft 44 and through the shaft 44. The aperture 46 allows cables 48 to run through the pan shaft 44 and between the yoke 22 and the base 12. The cables 48 can include control and power cables for the light source 18 and/or motors, sensors, or other similar items associated with the apparatus 10. It is desirable to limit the rotation of the light fixture 14 relative to the base 12 so that the cables 48 do not twist more than a desired amount (e.g., do not twist more than 500 degrees). Accordingly, the bearing 42 also includes a rotational stop, discussed below.

The bearing 42 includes a first race 50, a second race 52, and a rolling element 54. The illustrated first race 50 is fixed. That is, the first face 50 is fixed from rotation relative to the base 12. The second race 52 is coupled to the pan shaft 44 for rotation with the pan shaft 44 about the pan axis 16. The rolling element 54 facilitates relative rotation between the races 50, 52. In the illustrated embodiment, the rolling element 54 includes a plurality of balls. In other embodiments, one or more balls may be used as the rolling elements and in yet other embodiments, other types of rolling elements may be utilized (e.g., cylindrical, spherical, tapered, needle, etc.).

The first race 50 includes a raceway 58. In some embodiments, the raceway 58 is machined or molded into the race 50. The raceway 58 is a curved such that the raceway 58 extends around the pan axis 16 and the shaft 44. In one embodiment, the raceway 58 extends at least 300 degrees around the pan axis 16. In another embodiment, the raceway 58 extends at least about 360 degrees or all the way around the pan axis 16/shaft 44. In yet another embodiment, the raceway 58 extends at least about 500 degrees around the pan axis 16. In the one embodiment, the raceway 58 extends at least about 540 degrees around the pan axis 16. In embodiments where the raceway 58 extends more than once (i.e., 360 degrees) around the pan axis 16, the raceway 58 defines a spiral as shown in FIG. 3 around the axis 16 and the shaft 44.

The raceway 58 includes a first end 60 and a second end 62. The rolling element 54 contacts the ends 60, 62 to act as stop and limit or inhibit relative rotation of the races 50, 52, which thereby limits rotation of the pan shaft 44 and rotation of the light fixture 14 about the pan axis 16. As discussed above, it is desirable in some embodiments to limit rotation of the light fixture 14. In the embodiment illustrated, the raceway 58 extends at least about 540 degrees around the pan axis 16. Therefore, rotation of the light fixture 14 about the pan axis 16 is limited to about 540 degrees. Actual rotation of the light fixture 14 is slightly less than 540 degrees due to length 64 of rolling element 54 and the degrees associated with the length 64. The allowed angle of rotation of the light fixture 14 may be easily adjusted in discrete steps by adding or removing rolling elements 54 to the raceway 58. Adding rolling elements 54 to the raceway 58 increases the length 64 of rolling element 54, which reduces the allowed angle of rotation of the light fixture 14. Removing rolling elements 54 from to the raceway 58 decreases the length 64 of rolling element 54, which reduces the allowed angle of rotation of the light fixture 14.

The second race 52 (FIG. 2) includes a recess 66 having end walls 67A and 67B. The rolling element 54 is held in the recess 66 between the end walls 67A, 67B and the first race 50. Therefore, the rolling element 54 remains in the recess 66 of the second race 52 during rotation of the light fixture 14 about the pan axis 16.

It has been found that the curved nature of the raceways 58 and the ends 60, 62 of the raceway 58 that form the rotational stop operate smoothly and with very little audible noise. It's desirable to limit noise so that those sitting by or near the light fixture panning apparatus 10 do not hear the apparatus 10 operating.

Referring to FIG. 1, the light fixture panning apparatus 10 further includes a pan motor 68 and pan transmission 70. The illustrated pan transmission 70 includes a drive pulley 74, a belt 76, and a driven pulley 78. The pan motor 68 is operable to rotate the pulley 74, which rotates pulley 78 via the belt 76 in order to rotate the light source 18 relative to base 12 about the pan axis 16. The illustrated panning apparatus 10 further includes a pan sensor 80. The pan sensor 80 determines rotational position of the light source 18. Also, the pan sensor 80 controls the pan motor 68 and stops the pan motor 68 so that the motor 68 does not over rotate the light fixture 14. That is, typically, the pan sensor 80 would stop rotation of the light fixture 14 before the rolling element 54 reaches the ends 60, 62 of the raceway 58. However, if for some reason the pan sensor 80 does not stop rotation of the light fixture 14, the rolling element 54 contacts an end 60, 62 of the raceway 58, which would cause the pan motor 68 to stall and stop rotation of the light fixture 14.

Various features and advantages of the invention are set forth in the following claims.

What is claimed is:

1. A light fixture panning apparatus comprising:

a base;

a light fixture rotatably coupled to the base such that the light fixture rotates about an axis relative to the base; and a bearing that facilitates rotation of the light fixture relative to the base about the axis, the bearing including a raceway and a rolling element that rolls along the raceway as the light fixture rotates about the axis relative to the base, wherein the raceway is curved such that the raceway extends around at least a portion of the axis.

2. The light fixture of claim 1, wherein the raceway extends at least 300 degrees around the axis.

3. The light fixture of claim 1, wherein the raceway extends at least 360 degrees around the axis.

4. The light fixture of claim 1, wherein the raceway extends at least 500 degrees around the axis.

5. The light fixture of claim 1, wherein the raceway defines a spiral.

6. The light fixture of claim 1, wherein the raceway includes a first end and a second end, wherein the rolling element contacts the first and second ends to inhibit rotation of the light fixture relative to the base about the axis.

7. The light fixture of claim 6, wherein the first end is spaced from the second end a distance to permit at least 360 degrees of rotation of the light fixture relative to the base about the axis.

8. The light fixture of claim 6, wherein the first end is spaced from the second end a distance to permit at least 500 degrees of rotation of the light fixture relative to the base about the axis.

9. The light fixture of claim 1, wherein the rolling element includes a ball.

10. The light fixture of claim 1, wherein the rolling element includes a plurality of balls.

11. The light fixture of claim 1, wherein the light fixture includes a light source and a mount.

12. The light fixture of claim 11, wherein the light source includes a light emitting diode (LED) light source.

13. The light fixture of claim 11, wherein the mount includes a yoke, wherein the light source is coupled to the yoke.

14. The light fixture of claim 11, wherein the axis is a pan axis, wherein the light source is rotatably coupled to the mount such that the light source rotates relative to the mount about a tilt axis.

15. The light fixture of claim 14, wherein the tilt axis is perpendicular to the pan axis.

16. The light fixture of claim 1, wherein the raceway is a first raceway, the bearing further including a second raceway, wherein the rolling element is between the first and second raceways such that the rolling element rolls along the first raceway and the second raceway.

17. The light fixture of claim 16, wherein the first raceway is fixed from rotation about the axis relative to the base and wherein the second raceway rotates about the axis relative to the base.

18. The light fixture of claim 1, further comprising a pan shaft that rotatably couples the light fixture to the base for rotation of the light fixture about the axis relative to the base.

19. The light fixture of claim 18, wherein the pan shaft is hollow includes an aperture extending along a length of the pan shaft, wherein a cable extends through the aperture.

20. The light figure of claim 18, wherein the axis extends centrally through the pan shaft.

* * * * *